US006322982B1

(12) United States Patent
Shyjan et al.

(10) Patent No.: US 6,322,982 B1
(45) Date of Patent: *Nov. 27, 2001

(54) MODULATION OF DRUG RESISTANCE VIA UBIQUITIN CARBOXY-TERMINAL HYDROLASE

(75) Inventors: Andrew W. Shyjan, Nahant; Kyle J. MacBeth, Boston, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/365,405

(22) Filed: Aug. 2, 1999

Related U.S. Application Data (62) Division of application No. 08/970,733, filed on Nov. 14, 1997, now Pat. No. 5,932,422.

(51) Int. Cl.[7] ............................ C12Q 1/68; C07H 21/04
(52) U.S. Cl. ................................. 435/6; 536/23.1
(58) Field of Search ................................. 435/6; 424/9.2; 536/23.1

(56) References Cited

U.S. PATENT DOCUMENTS

| 4,740,463 | 4/1988 | Weinberg et al. ................ 180/247 |
| 5,545,806 | 8/1996 | Lonberg et al. ................... 800/6 |
| 5,569,825 | 10/1996 | Lonberg et al. ................ 435/320.1 |

OTHER PUBLICATIONS

Gura, T. Systems for identifying new drugs are often faulty. Science. vol. 278:1041–1042, Nov. 1997.*
Batist et al; J. Biol. Chem. 261:15544–15549 (1986), Overexpression of a Novel Anionic Glutathione Transferase in Multidrug–resistant Human Breast Cancer Cells.
Bird; Science 242:423–426 (1988), Single–Chain Antigen–Binding Proteins.
Day et al., FEBS Lett., 210:157–160 (1987), Molecular cloning of cDNA coding for human PGP 9.5 protein.
Egholm et al., Nature 365:566–568 (1993), PNA hybridizes to complementary oligonucleotides obeying the Watson–Crick hydrogen–bonding rules.
Hamilton et al., Semin. Oncol. 11:285–298 (1984), Experimental Model Systems of Ovarian Cancer: Applications to the Design and Evaluation of New . . . .
Helene et al., Ann. N.Y. Acad. Sci. 660:27–36 (1992), Control of Gene Expression by Triple Helix–Forming Oligonucleotides.
Hershko et al., Ann. Rev. Biochem. 61:761–807 (1992), The Ubiquitin System for Protein Degradation.
Jentsch et al., Biochim. Biophys. Acta 1089:127–139 (1991), Genetic analysis of the ubiquitin system.
Kohler et al., Nature 256:495–497 (1975), Continuous cultures of fused cells secreting antibody of predefined specificity.
Letsinger et al., Proc. Natl. Acad. Sci. USA 86:6553–6556 (1989), Cholesteryl–conjugated oligonucleotides: Synthesis, properties, and activity as inhibitors of . . . .
Maki et al., Differentiation 60:59–66 (1996), Role of ubiquitin carboxyl terminal hydrolase in the differentiation of human acute lymphoblastic . . . .
Mayer et al., Biochim. Biophys. Acta 1089:141–157 (1991), Ubiquitin in health and disease.
Mirski et al., Cancer Res. 47:2594–2598 (1987), Multidrug Resistance in a Human Small Cell Lung Cancer Cell Line Selected in Adriamycin.
Papa et al., Nature 366:313–319 (1993), The yeast DOA4 gene encodes a deubiquitinating enzyme related to a product of the human tre–2 oncogene.
Sarver et al., Science 247:1222–1225 (1990), Ribozymes as Potential Anti–HIV–1 Therapeutic Agents.
Takeda et al., Nature 314:452–454 (1985), Construction of chimaeric processed immunoglobulin genes containing mouse variable and human constant . . . .
Tobias et al., J. Biol. Chem. 266:12021–12028 (1991), Cloning and Functional Analysis of the Ubiquitin–specific Protease Gene UBP1 of *Saccharomyces cerevisiae*.
Wilkinson et al., Science 246:670 (1989), Neuron–Specific Protein PGP 9.5 is a Ubiquitin Carboxyl–Terminal Hydrolase.
Woo et al., J. Biol. Chem. 270:18766–18773 (1995), Multiple Ubiquitin C–terminal Hydrolases from Chick Skeletal Muscle.
Zhang et al., Dev. Biol. 157:214–223 (1993), Cloning and Analysis of Expression of a Ubiquitin Carboxyl Terminal Hydrolase Expressed during . . . .

* cited by examiner

*Primary Examiner*—Terry McKelvey
*Assistant Examiner*—William Sandals
(74) *Attorney, Agent, or Firm*—Fish & Richardson P.C.

(57) ABSTRACT

The expression of ubiquitin carboxy-terminal hydrolase is aberrant in cells that are resistant to treatment with chemical agents. Accordingly, the invention features methods for diagnosing and treating drug resistant cells (e.g., tumor cells) by examining and modulating the expression or activity of UCH

16 Claims, 2 Drawing Sheets

MODULATION OF DRUG RESISTANCE VIA UBIQUITIN CARBOXY-TERMINAL HYDROLASE

RELATED APPLICATION INFORMATION

This application is a divisional of application Ser. No. 08/970,733, filed Nov. 14, 1997 now U.S. Pat. No. 5,932,422.

BACKGROUND OF THE INVENTION

The field of the invention is modulation of drug resistance.

The concentrations of proteins in biological cells are regulated by elegant biochemical mechanisms. By way of these mechanisms, cells eliminate damaged proteins and can, by altering the concentrations of biologically active proteins, such as enzymes, alter cellular processes that are important for the overall well being of the organism.

In eukaryotic cells, proteins can be selectively degraded via the ubiquitin pathway. Ubiquitin is a highly conserved protein that is covalently ligated to proteins in a process referred to as ubiquitination. Proteins that have been ubiquitinated are committed to degradation by a 26S protease complex. The ubiquitin pathway is thought to play an important role in regulating cellular processes by regulating protein levels. Numerous review articles have described various aspects of the ubiquitin pathway. For example, the molecular genetics of the ubiquitin system have been reviewed by Finley et al. (*Ann. Rev. Cell Biol.* 7:25–69, 1991) and Jentsch et al. (*Biochim. Biophys. Acta* 1089:127–139, 1991); the involvement of the system in pathological states has been reviewed by Mayer et al. (*Biochim. Biophys. Acta* 1089:141–157, 1991); and the biochemistry and enzymology of various stages of the ubiquitin pathway have been reviewed by Hershko and Ciechanover (*Ann. Rev. Biochem.* 61:761–807, 1992). Interest in the ubiquitin pathway is due in part to the wide variety of physiological processes that are affected by ubiquitination of proteins. These processes include the heat shock response, DNA repair, cell cycle progression, the modification of histones and of receptors, and the possible pathogenesis of selected neurodegenerative diseases.

Only the protein conjugated to ubiquitin is degraded via the proteasome; ubiquitin itself is recycled by ubiquitin carboxy-terminal hydrolases, which cleave the bond between ubiquitin and the protein targeted for degradation. These enzymes constitute a family of thiol proteases, and homologues have been found in, for example, yeast (Miller et al., *BioTechnology* 7:698–704, 1989; Tobias and Varshavsky, *J. Biol. Chem.* 266:12021–12028, 1991; Baker et al., *J. Biol. Chem.* 267:23364–23375, 1992), bovine (Papa and Hochstrasser, *Nature* 366:313–319, 1993), avian (Woo et al., *J. Biol. Chem.* 270:18766–18773, 1995), Drosophila (Zhang et al., *Dev. Biol.* 17:214, 1993) and human (Wilkinson et al., *Science* 246:670, 1989) cells.

SUMMARY OF THE INVENTION

As described herein for the first time, the expression of ubiquitin carboxy-terminal hydrolase (UCH; sometimes abbreviated UCTH) is aberrant in cells that are resistant to treatment with chemical agents, for example, pharmaceutical agents. Accordingly, the invention features methods for diagnosing and treating drug resistant cells (e.g., tumor cells) by examining and modulating the expression or activity of UCH. The cells can be resistant to one or more pharmaceutical agents, and so may, as appropriate, be referred to as drug resistant or multidrug resistant cells.

The present invention provides a method of assessing expression, especially aberrant expression, of a cellular UCH gene, which may indicate the presence, persistence, or reappearance of tumor cells in an individual's tissue. UCH gene expression is assessed by obtaining a sample of cellular tissue from a mammal (e.g., a human), preferably from a site in the body suspected of containing malignant tissue, and obtaining RNA from the tissue. The RNA is combined with a UCH oligonucleotide under standard conditions for hybridization, and the resulting mixture is assayed for the presence of hybrids consisting of the UCH oligonucleotide and a cellular UCH gene transcript. As further described below, the oligonucleotide can be detectably labeled or otherwise modified. For example, the oligonucleotide can have a peptide-nucleic acid backbone. The presence and/or relative abundance of hybrids indicates aberrant expression of a cellular UCH gene, and correlates with the occurrence of transformed cells in situ, especially transformed cells having a drug-resistant phenotype.

Information obtained by practicing the diagnostic methods described herein will be useful in determining the prognosis for patients with malignancies (tumors) that are characterized by expression of UCH and thus by a drug-resistance phenotype. The information will also assist the clinician in designing chemotherapeutic or other treatment regimes to eradicate such malignancies from the body. The methods described herein can be practiced with a sample of any body tissue type, such as that from the mammary, respiratory, urogenital, endocrine, or immune systems. The present methods are particularly useful in assessing biopsy tissue obtained from the breast, respiratory system (e.g., by bronchoalveolar lavage), ovary, uterus, cervix, prostate, testes, pancreas, spleen, bone marrow, or lymphatic system.

In addition, the invention features therapeutic compositions, such as those containing a compound that modulates expression of UCH protein, and therapeutic methods in which these compounds are administered to a patient. Accordingly, the invention provides means for mitigating (detectably decreasing or otherwise affecting) aberrant expression of a UCH gene or protein, and for attenuating an undesirable drug-resistance phenotype, particularly a phenotype contributed by UCH. More particularly, the invention features methods for mitigating aberrant expression of a UCH gene, and/or aberrant activation or alteration of a UCH polypeptide. One embodiment involves the administration of a pharmaceutical composition containing an antisense UCH oligonucleotide to a mammal suffering from the effects of altered expression and/or function of UCH. Another embodiment involves the administration of an antibody or fusion polypeptide that specifically binds UCH. In either embodiment, the therapeutic agent is administered systemically or locally under conditions sufficient to mitigate or attenuate the phenotype associated with aberrant expression or activity of UCH (including undesirably high or undesirably low levels of UCH expression or activity). Preferably, the therapeutic agent is administered under conditions sufficient to destroy cells producing aberrant levels or UCH or cells in which the activity of UCH is higher than that in a comparably cell. For example, either of the foregoing therapeutic agents can be administered as an adjunct to conventional chemotherapy. That is, either of the foregoing therapeutic agents can be coadministered together with one or more chemotherapeutic drugs. In this manner, the invention provides for destruction of drug-resistant tumor cells in situ. The present antisense or fusion polypeptide therapeutic agent can be administered prior to, concomitant with, or following administration of one or more chemotherapeutic drugs. In such embodiments, the antisense pharmaceutical composition mitigates resistance of UCH-expressing cells to the cytotoxic effects of the chemotherapeutic drug. That is, the antisense composition attenuates the phenotype associated with an aberrant level of UCH expression or activity, which is characterized by the property of drug resistance. This is accomplished by disrupting activation or transcription of the UCH gene, or by destabilizing RNA transcripts thereof. Diminished or discontinued expression of UCH renders cells more susceptible to the cytotoxic effects of a chemotherapeutic drug. Similarly, a therapeutically administered cytotoxic fusion polypeptide localized in the vicinity of cells aberrantly expressing UCH can produce cytolysis thereof. Alternatively (or in addition), a chemoattractant fusion polypeptide localized to UCH-expressing cells can stimulate their destruction by macrophages, killer T cells, or cytotoxic T cells.

Another aspect of the invention features methods for identifying a modulator of UCH. In general, this aspect of the invention relies on the use of a UCH-expressing host cell. Prokaryotic or eukaryotic host cells can be used for purposes of identifying a UCH inhibitor. However, in general, eukaryotic host cells are preferred. Yeast or mammalian cells can be used, as desired or as dictated by specific circumstances, as can plant cells. Presently, mammalian host cells, particularly human cells are preferred. The UCH-expressing host cell is contacted with a candidate modulator, and after a sufficient period of time for modulatory effects (inhibition or stimulation) to be manifested, the cell is assayed to determine whether the candidate modulator indeed affects UCH. In one embodiment, the level of cellular UCH gene expression is assayed. A detectable decrease in (attenuation or abrogation) or cessation of UCH gene expression indicates that the candidate modulator is a UCH inhibitor. Another embodiment involves assay of the amount or rate of production of UCH polypeptide by the cell. A detectable decrease or cessation of immunologically recognized UCH polypeptide indicates that the candidate modulator is a UCH inhibitor. In another embodiment, the host cell is contacted with a substrate (e.g., a cytotoxin) degraded by the ubiquitin pathway. The candidate inhibitor is contacted with the host cell prior to, concomitantly with, or following exposure to the substrate. The amount of substrate degraded by the cell is assessed. A detectable decrease in degradation of the substrate indicates that the candidate is a UCH inhibitor. Alternatively, in specific embodiments wherein the substrate is cytotoxic, survival of the host cell is assessed. A detectable decrease in survival indicates that the candidate is an UCH inhibitor. Candidate substances appropriate for screening as UCH modulators in any of the foregoing embodiments include natural or synthetic metabolites, toxins, antibiotics, elements of a combinatorial chemistry, nucleotide, or peptide library, naturally sourced cell secretion products, cell lysates, and the like.

An additional aspect of the invention features a UCH modulator identified by any of the above-described methods. Preferably, the modulator is a small molecule, for example, an element of a combinatorial chemistry library or a low molecular weight natural or synthetic product or metabolite. The modulator may be dispersed in a pharmaceutically acceptable vehicle to produce a drug-resistance attenuating pharmaceutical composition of the present invention.

Another aspect of the invention thus features inhibitor-based methods of mitigating aberrant UCH expression and/or polypeptide production. The present method involves the step of administering a UCH inhibitor, optionally dispersed in a pharmaceutically acceptable vehicle to a mammal suffering from effects of a UCH-associated aberrancy. In a preferred embodiment, the invention provides a method for improving (potentiating) effectiveness of chemotherapy to eradicate UCH-expressing cells, for example, drug-resistant transformed cells, from the body of a mammal. This method involves the steps of administering a chemotherapeutic drug to the mammal, and coadministering a UCH inhibitor identified as described herein. Preferably, the inhibitor is provided in the form of a drug-resistance attenuating composition, i.e., dispersed in a pharmaceutically acceptable vehicle. This method is particularly preferred where a chemotherapy adjunct is desired to eradicate drug-resistant tumor cells.

Advantageously, the method can be practiced where a fluid tumor (e.g., leukemia, lymphoma, lymphosarcoma or ascites) is present, or where the situs of a primary or metastatic tumor is deemed unsuitable for surgical intervention or, especially, where a remontant or reemergent tumor is observed following an initial course of chemotherapeutic treatment.

The term "modulation" as used herein refers to both upregulation (i.e., activation or stimulation), for example by agonizing, and downregulation (i.e., inhibition or suppression), for example by antagonizing of a bioactivity (e.g., expression of a gene).

The term "an aberrant activity" or "abnormal activity," as applied to an activity of a protein, refers to an activity which differs from the activity of the wild-type or native protein or which differs from the activity of the protein in a healthy subject. An activity of a protein can be aberrant because it is stronger than the activity of its native counterpart. Alternatively, an activity can be aberrant because it is weaker or absent relative to the activity of its native counterpart. An aberrant activity can also be a change in an activity. For example, an aberrant protein can interact with a different protein relative to its native counterpart. A cell can have an aberrant activity due to overexpression or underexpression of the gene encoding UCH.

"Biological activity" or "bioactivity" or "activity" or "biological function," which are used interchangeably for the purposes herein, when applied to UCH, mean an effector or antigenic function that is directly or indirectly performed by a UCH polypeptide (whether in its native or denatured conformation), or by any fragment thereof. A biological activity is also intended to include binding to a protein, such as binding to a domain of UCH. UCH bioactivity can be modulated by directly affecting UCH protein. Alternatively, UCH bioactivity can be modulated by modulating the level of UCH protein, such as by modulating expression of a UCH gene. Antigenic functions include possession of an epitope or antigenic site that is capable of cross-reacting with antibodies raised against a naturally occurring or denatured UCH polypeptide or fragment thereof.

The term "treating" as used herein is intended to encompass curing as well as ameliorating at least one symptom of a condition or disease.

Unless otherwise defined, all technical and scientific terms used herein have the same meaning as commonly understood by one of ordinary skill in the art to which this invention belongs. Preferred materials and methods are described below. However, those of ordinary skill in the art will understand that materials and methods that are similar or equivalent to those described herein can be used in the practice or testing of the present invention.

All publications, patent applications, patents, and other references other than internet URLS mentioned herein are incorporated by reference to their entirety. Features and advantages of the invention will be apparent from the following detailed description, and from the claims.

DETAILED DESCRIPTION

Mammalian cells having a "drug-resistant" or "multidrug-resistant" phenotype are characterized by the ability to export or expel or otherwise desa plurality of cytotoxic substances (e.g., chemotherapeutic drugs) from the intracellular milieu. Cells can acquire this phenotype as a result of selection pressure imposed by exposure to a single chemotherapeutic drug (the selection toxin). Alternatively, cells may exhibit the phenotype prior to toxin exposure, since the export of cytotoxic substances may involve a mechanism in common with normal export of cellular secretion products, metabolites, and the like. Multidrug resistance differs from simple acquired resistance to the selection toxin in that the cell acquires competence to export or otherwise dispose of additional cytotoxins (other chemotherapeutic drugs) to which the cell was not previously exposed. For example, a multidrug-resistance cell population was isolated by culturing the H69 cell line, derived from a human small cell lung carcinoma, in the presence of adriamycin as a selection toxin (Mirski et al., *Cancer Res.* 47:2594–2598, 1987).

As shown in the example below; UCH is highly expressed in cells that are resistant to cytotoxic agents. A cell is said to be resistant to a cytotoxic agent if it is unaffected by that agent, or less affected than a similar cell (e.g., a transformed cell of a given phenotype may be less affected than a non-transformed cell of the same phenotype). It follows that one can predict whether a cell will be resistant to treatment with a chemical agent by examining the level of UCH expression or activity, and further, that one can modulate cellular resistance to chemical agents by altering the expression or activity of UCH.

Monitoring UCH protein production or gene expression levels, or fluctuations therein, in one or more tumor biopsy samples will provide information relevant to the diagnosis, prognosis and/or staging of neoplastic disease in a cancer sufferer. Any suitable means for detecting UCH protein production or gene expression can be applied. Preferably, diagnosis is achieved by hybridization techniques involving the use of a modified UCH probe, as further described below. A particularly preferred technique involves the use of a peptide-nucleic acid probe as described, for example in Egholm et al. (*Nature* 365:566–568, 1993) and Perry-O'Keefe et al. (*Proc. Natl. Acad. Sci. USA* 93:14670–14675, 1996).

A Wide Variety of Cell Types are Amenable to the Diagnostic and Therapeutic Methods Described Herein The diagnostic and therapeutic methods described below can be applied to any cell that expresses UCH, i.e., to any eukaryotic cell. Furthermore, any cell type that can be made either more or less resistant to a chemical agent by altering the level of UCH expression or activity can be used in the practice of the invention. A wide variety of cell types are encompassed because UCH is an essential and highly conserved enzyme that functions in a fundamental biochemical pathway used by all eukaryotic cells.

The cell types used in the practice of the invention can be, for example, fungal cells (such as a yeast cell), plant cells (such as those of an edible crop, a fruit-bearing tree, or a decorative plant), or higher eukaryotic cells (such as the cells of a mammal) that exhibit an altered response to a fungicide, herbicide, or chemotherapeutic agent, respectively.

Furthermore, mammalian cells that are amenable to the diagnostic and therapeutic methods described herein include a wide variety of cell types that proliferate uncontrollably and thereby give rise various cancers. For example, the diagnostic and therapeutic methods of the invention can be applied to cancerous cells of mesenchymal origin, such as those producing sarcomas (e.g., fibrosarcoma, myxosarcoma, liposarcoma, chondrosarcoma, osteogenic sarcoma or chordosarcoma, angiosarcoma, endotheliosarcoma, lymphangiosarcoma, synoviosarcoma or mesotheliosarcoma); leukemias and lymphomas such as granulocytic leukemia, monocytic leukemia, lymphocytic leukemia, malignant lymphoma, plasmocytoma, reticulum cell sarcoma, or Hodgkins disease; sarcomas such as leiomysarcoma or rhabdomysarcoma, tumors of epithelial origin such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, or embryonal carcinoma; and tumors of the nervous system including glioma, meningoma, medulloblastoma, schwannoma or epidymoma. Additional cell types amenable to diagnosis and treatment according to the methods described herein include those giving rise to mammary carcinomas, gastrointestinal carcinoma, such a colonic carcinomas, bladder carcinoma, prostate carcinoma, and squamous cell carcinoma of the neck and head region. The diagnostic and therapeutic methods of the invention can be carried out using a mammary cell, or a cell in the respiratory, urogenital, endocrine, or immune system.

Diagnostic Assays: Resistance to Chemical Agents Can be Correlated with UCH Expression or Activity Determining the most effective therapeutic regime for a particular disease of condition can be difficult. For example, patients who have developed a cancer or other disease associated with the proliferative growth of cells must, together with their physician, decide between treatment regimes that are based on chemotherapy, radiation therapy, or surgery. It would, therefore, be useful to determine whether the proliferating cells are likely to be resistant or sensitive to chemotherapeutic agents. The discovery that UCH is upregulated in drug resistant cells provides the basis for diagnostic methods that can be used to determine whether the cells affected in any given disease or condition are likely to be resistant to chemical agents. The method can be carried out, for example, by assessing the expression or activity of UCH in the cells in question. An elevated level of expression or activity (for example, in comparison with the level of expression or activity in a non-tumor cell) would indicate the presence of a disease or condition in which cells are resistant to chemical agents, such as chemotherapeutic agents. Conversely, a normal or low level of expression or activity would indicate the presence of a disease or condition in which cells are sensitive to chemical agents.

To perform the diagnostic methods, a sample of tissue is first obtained. The most appropriate tissues to be sampled, when given a particular set of symptoms, are known to those of skill in the art of medicine, particularly those who routinely diagnose and treat patients with cancer. The sample itself can be any sample containing diseased cells, such as a blood, urine, serum, or plasma sample. Alternatively, the sample can be a tissue sample (e.g., biopsy tissue), or an effusion obtained from a joint (e.g., synovial fluid), from the abdominal cavity (e.g., ascites fluid), from the chest (e.g., pleural fluid), from the central nervous system (e.g., cerebral spinal fluid), or from the eye (e.g., aqueous humor). The sample can also consist of cultured cells that were originally obtained from a patient (e.g., peripheral blood mononuclear cells). In many instances, the sample will be obtained from a human patient, but can also be obtained from a plant, or from an animal that is valued for commercial worth (e.g., a cow, sheep, or pig), for athletic performance (e.g., dogs or horses that race), or for companionship (e.g., a cat, dog, or other pet).

Those of skill in the art are readily able to determine whether cells within a sample contain a normal or aberrant amount of UCH, and whether that expression correlates with an increased resistance to the action of a chemical agent. This determination can be made by following the protocol set forth in the example below, in which RNA is harvested from cells that have an undesirably high level of resistance to a chemotherapeutic agent and is assessed by Northern blot analysis. Alternatively, the level of UCH gene expression can be assessed by performing a quantitative PCR-based assay (the experimental basis being set forth in Mullis, K. B., 1987, U.S. Pat. No. 4,683,202), an RNAse protection assay, or in situ hybridization.

To obtain a probe suitable for assessing UCH mRNA expression, those of ordinary skill in the art can obtain the known sequence of a UCH-encoding nucleic acid molecule from publications (e.g., see Day et al., FEBS Lett. 210:157–160, 1987) or by searching the GenBank database. To move directly to the sequence of a human mRNA for UCH (formerly referred to as protein gene product (PGP) 9.5), those of ordinary skill in the art can search GenBank using the Accession Number X04741.

If desired, the expression of UCH can also be assessed at the level of translation, where UCH protein, rather than the mRNA encoding it, is analyzed. Typically, protein expression is analyzed by Western blot analysis or, in situ, by immunohistochemistry. Alternatively, the activity of UCH can be assessed in vitro, for example by performing assays analogous to those described by Woo et al. in assessing UCHs isolated from chick skeletal muscle (*J. Biol. Chem.* 270:18766–18733, 1995).

The levels of UCH expression or activity in cells collected from a patient can be compared with cells harvested from a non-affected region of the patient's body, or from a healthy individual. Cells within a sample (e.g., malignant cells within biopsy tissue) that overexpress UCH are likely to be resistant to chemotherapeutic agents. In this circumstance, the level of UCH expression or activity can be altered, as described below, in order to alter the resistance of the cell to chemotherapeutic agents: lowering the level of UCH expression or activity should lower the resistance of the cell to therapeutic agents.

Furthermore, two or more biopsy samples can be obtained from an individual (e.g., a cancer sufferer) and assessed at different times. For example, a first biopsy sample corresponds to a time of diagnosis or to a time prior to or concomitant with the onset of chemotherapy, and a second biopsy sample can correspond to a timepoint at which beneficial results of chemotherapy are expected to be detectable (e.g., a time sufficiently remote from the onset of chemotherapy for cytotoxic effects to be observed). One or more subsequent biopsy samples may correspond to further timepoints optionally correlated with fluctuations in clinical parameters (e.g., relapse, remission, a change in disease staging, or the like). Changes in UCH expression are expected to correlate with, or to predict, the emergence or attenuation of a drug-resistance phenotype.

It sill be appreciated that the causes of drug-resistance phenotypes vary with each individual cell type and may not be wholly accounted for by expression or overexpression of UCH.

Decreasing the Resistance of a Cell to a Chemical Agent

The resistance of a cell to a chemical agent can be lowered (i.e., the cell can be made more sensitive to the effects of a chemical agent, such as a pharmaceutical agent), by decreasing the expression or activity of UCH.

Skilled artisans are readily able to determine the circumstances in which it would be desirable to decrease the resistance of a cell to a cytotoxic or otherwise deleterious chemical agent. Generally, these circumstances include any situation in which it is desirable to treat a cell with a chemical agent that is otherwise ineffective. For example, it would be desirable to lower the resistance of cancerous cells to chemotherapeutic agents in order to more effectively treat the cancer. The resistance may be lowered in any cell, regardless of the level of expression of UCH. Thus, cells that express normal levels of UCH are also candidates for treatment.

Decreasing UCH Expression with Antisense Oligonucleotides

Therapeutic methods that are based on the administration of antisense oligonucleotides require synthesis of oligonucleotides (either DNA or RNA) that are complementary to UCH mRNA molecules; the antisense oligonucleotides will specifically bind to the complementary UCH mRNA transcripts and prevent translation.

Absolute complementary, although preferred, is not required. A sequence "complementarity" to a portion of an RNA, as referred to herein, means a sequence having sufficient complementarity to be able to hybridize with the RNA, forming a stable duplex; in the case of double-stranded antisense nucleic acid molecules, a single strand of the duplex DNA may thus be tested, or triplex formation may be assayed. The ability to hybridize will depend on both the degree of complementarity and the length of the antisense nucleic acid. Generally, longer antisense oligonucleotides can contain mismatches with their targets yet still form a stable duplex (or triplex, as the case may be). One of ordinary skill in the art can ascertain a tolerable degree of mismatch by using standard procedures to determine the melting point of the hybridized complex. Antisense oligonucleotides complementary to mRNA coding regions are less efficient inhibitors of translation than oligonucleotides that are complementary to 5'- or 3'-untranslated sequence, but could be used in accordance with the instant invention. The antisense nucleic acids should be at least six nucleotides in length, and are preferably oligonucleotides ranging from 6 to about 50 nucleotides in length. In specific aspects, the oligonucleotide is at least 10 nucleotides, preferably at least 17 nucleotides, more preferably at least 25 nucleotides, and most preferably at least 50 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same lengths as the test oligonucleotide and that the nucleotide sequence of the oligonucleotide differs from the antisense sequence no more than is necessary to prevent specific hybridization to the target sequence.

The oligonucleotide can be modified at the base moiety, sugar moiety, or phosphate backbone, for example, to improve stability of the molecule, hybridization, etc. The oligonucleotide may include other appended groups such as peptides (for example, for targeting host cell receptors in vivo), or agents facilitating transport across the cell membrane (see, for example, Letsinger et al., *Proc. Natl. Acad. Sci. USA* 86:6553–6556, 1989; Lemaitre et al., *Proc. Natl. Acad. Sci. USA* 84:648–652, 1987; PCT Publication No. WO88/09810, published Dec. 15, 1988), or the blood-brain barrier (see, for example, PCT Publication No. WO89/10134, published Apr. 25, 1988), hybridization-triggered cleavage agents, (see, for example, Krol et al., *BioTechniques* 6:958–976, 1988) or intercalating agents (see, for example, Zon, *Pharm. Res.* 5:539–549, 1988). To this end, the oligonucleotide can be conjugated to another molecule, for example, a peptide, hybridization triggered cross-linking agent, transport agent, hybridization-triggered cleavage agent, and the like.

The antisense oligonucleotide may comprise at least one modified base moiety that is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625–6641, 1987). The oligonucleotide can be a 2'-0-methylribonucleotide (Inoue et al., *Nucl. Acids Res.* 15:16131–6148, 1987), or a chimeric RNA-DNA analogue (Inoue et al., *FEBS Lett.* 215:327–330, 1987).

Oligonucleotides used in the practice of the invention can be synthesized by standard methods known in the art, for example, by use of an automated DNA synthesizer (such as are commercially available from Biosearch, Applied Biosystems, etc.). As examples, phosphorothioate oligonucleotides can be synthesized by the method of Stein et al. (*Nucl. Acids Res.* 16:3209, 1988), and methylphosphonate oligonucleotides can be prepared by use of controlled pore glass polymer supports (Sarin et al., *Proc. Natl. Acad. Sci. USA* 85:7448–7451, 1988).

The antisense molecules would be delivered to cells that overexpress UCH in vivo. A number of methods have been developed for delivering antisense DNA or RNA to cells; for example, antisense molecules can be injected directly into the tissue site. Alternatively, modified antisense molecules have been designed that target the desired cells (for example, antisense molecules can be linked to peptides or antibodies that specifically bind receptors or antigens expressed on the target cell surface). These target specific molecules can be administered systematically.

It can be difficult to achieve intracellular concentrations of antisense molecules that are sufficient to suppress translation of endogenous mRNAs. Therefore, a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous UCH transcripts and thereby prevent translation of UCH mRNA. For example, a vector can be introduced in vivo such that it is taken up by a cell and directs the transcription of an anitsense RNA. Such a vector can remain episomal or become chromosomally integrated, as long as it can be transcribed to produce the desired antisense RNA.

Methods of designing antisense oligonucleotides and introducing them into hose cells have been described in, for example, Weinberg et al. (U.S. Pat. No. 4,740,463; hereby incorporated by reference). For an antisense oligonucleotide that has been demonstrated to specifically inhibit UCH expression, see Maki et al. (*Differentiation* 60:59–66, 1996).

Decreasing UCH Expression with Ribozyme Molecules

Ribozyme molecules designed to catalytically cleave UCH mRNA transcripts can also be used to prevent translation of UCH mRNA and expression of UCH. (See, e.g., PCT International Publication WO90/11364, published Oct. 4, 1990; Sarver et al., *Science* 247:1222–1225, 1990). While ribozymes that cleave mRNA at site specific recognition sequences can be used to destroy UCH mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591, 1988. There are many potential hammerhead ribozyme cleavage sites within the nucleotide sequence of human UCH cDNA. Preferably, the ribozyme is engineered so that the cleavage recognition site is located near the 5' end of the UCH mRNA; i.e., to increase efficiency and minimize the intracellular accumulation of non-functional mRNA transcripts.

Ribozymes useful in the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborates (Zaug et al., *Science* 224:574–578, 1984; Zaug and Cech, *Science* 231:470–475, 1986; Zaug et al., *Nature* 324:429–433, 1986; published International patent application No. WO 88/04300 by University Patents Inc.; Been and Cech, *Cell* 47:207–216, 1986). The Cech-type ribozymes have an eight basepair active site that hybridizes to a target RNA sequence, whereafter cleavage of the target RNA takes place.

As in the antisense approach, the ribozymes can be composed of modified oligonucleotides (e.g. for improved stability, targeting, etc.) and should be delivered to cells that express UCH in vivo, for example, cells within a tumor or benign growth. A preferred method of delivery involves using a DNA construct "encoding" the ribozyme under the control of a strong constitutive pol III or pol II promoter, so that transfected cells will produce sufficient quantities of the ribozyme to destroy endogenous UCH messages and inhibit translation. Because ribozymes, unlike antisense molecules, are catalytic, a lower intracellular concentration is required for efficiency.

Decreasing UCH Expression by Homologous Recombination

Endogenous UCH gene expression can also be reduced by inactivating or "knocking out" the UCH gene or its promoter using targeted homologous recombination (e.g., see Smithies et al., *Nature* 317:230–234, 1985; Thomas and Capecchi, *Cell* 51:503–512, 1987; Thompson et al., *Cell* 5:313–321, 1989). For example, a mutant, non-functional UCH (or a completely unrelated DNA sequence) flanked by DNA homologous to the endogenous UCH gene (either the coding regions or regulatory regions) can be used, with or without a selectable marker and/or a negative selectable marker, to transfect cells that express UCH in vivo. Insertion of the DNA construct, via targeted homologous recombination, results in inactivation of the UCH gene. The recombinant DNA constructs can be directly administered or targeted to the required site in vivo using appropriate viral vectors, for example, herpes virus vectors for delivery to brain tissue, where inoperable tumors can arise.

Alternatively, endogenous UCH gene expression can be reduced by targeting deoxyribonucleotide sequences complementary to the regulator region of the UCH gene (i.e., the UCH promoter and/or enhancers) to form triple helical structures that prevent transcription of the UCH gene in target cells in the body. (See generally, Helene, *Anticancer Drug Des.* 6:569–84, 1991; Helene et al., *Ann. N.Y. Acad. Sci.* 660:27–36, 1989; and Maher, *Bioassays* 14:807–15, 1992).

Decreasing UCH Activity with Antibodies or Chemical Compounds

The invention can also be practiced using antibodies that specifically bind UCH. Antibodies that specifically recognize one or more epitopes of UCH enzymes include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

Antibodies can be used, for example, to detect UCH in a biological sample and may, therefore, be utilized as part of a diagnostic or prognostic technique whereby patients may be tested for abnormal amounts of UCH (as described above). Additionally, such antibodies can be used in conjunction with gene therapy techniques to, for example, evaluate cells expressing UCH following transfection with a UCH-encoding nucleic acid sequence. Preferably, the antibodies recognize epitopes of UCH that are unique, i.e., are not present on other proteins, even if those proteins function in the ubiquitin pathway or are otherwise related to UCH.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein (*Nature* 256:495–497, 1975; and U.S. Pat. No. 4,376,110), the human B cell hybridoma technique (Kosbor et al., *Immunology Today* 4:72, 1983; Cole et al., *Proc. Natl. Acad. Sci. USA* 80:2026–2030, 1983), and the EBV-hybridoma technique (Cole et al., "Monoclonal Antibodies And Cancer Therapy," Alan R. Liss, Inc. pp. 77–96, 1985). Such antibodies may be of any immunoglobulin class including IgG, IgM, IgE, IgA, IgD and any subclass thereof. The hybridoma producing mAbs useful in the practice of this invention can be cultivated in vitro or in vivo. Due to production of high titers or mAbs, in vivo production is generally preferred.

In addition, techniques developed for the production of "chimeric antibodies" (Morrison et al., *Proc. Natl. Acad. Sci. USA* 81:6851–6855, 1984; Neuberger et al., *Nature* 312:604–608, 1984; Takeda et al., *Nature* 314:452–454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423–426, 1988; Huston et al., *Proc. Natl. Acad. Sci. USA* 85:5879–5883, 1988; and Ward et al., 1989, *Nature* 334:544–546, 1989) can be adapted to produce single chain antibodies against UCH gene products. Single chain antibodies are formed by linking the heavy and light chain fragments of the Fv region via an amino acid bridge, resulting in a single chain polypeptide.

Antibody fragments that recognize specific epitopes can be generated by known techniques. These fragments include but are not limited to: the F(ab')$_2$ fragments which can be produced by pepsin digestion of the antibody molecule, and the Fab fragments which can be generated by reducing the disulfide bridges of the F(ab')$_2$ fragments. Alternatively, Fab expression libraries may be constructed (Huse et al., *Science* 246:1275–1281, 1989) to allow rapid and easy identification of monoclonal Fab fragments with the desired specificity. These antibodies can, in turn, be utilized to generate anti-idiotype antibodies that "mimic" UCH, using techniques well known to those skilled in the art. (See, for example, Greenspan and Bona, *FASEB J.* 7:437–444, 1993; and Nissinoff, *J. Immunol.* 147:2429–2438, 1991).

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., *Nature Genetics* 7:13–21, 1994; see also U.S. Pat. Nos. 5,545,806 and 5,569,825, both of which are hereby incorporated by reference).

The methods described herein may be performed, for example, by utilizing pre-packaged kits comprising at least one specific UCH nucleotide sequence or antibody reagent described herein, which may be conveniently used, for example, in clinical settings, to diagnose and treat conditions associated with an increased (or decreased) resistance to chemical agents.

The activity of UCH can be decreased with chemical compounds such as sodium borohydrate, and sulfhydryl blocking agent such as iodoacetamide. However, it is more likely that small molecules, for example those identified by the screening methods described herein, will be clinically useful.

Increasing the Resistance of a Cell to a Chemical Agent

The resistance of a cell to a chemical agent can be increased (i.e., the cell can be made less sensitive to the effects of the agent), by increasing the expression or activity of UCH. The effects of the chemical agent can be, but are not necessarily, deleterious to the cell. Chemical agents that can be used in the practice of the invention are described more fully below. A cell will be made more resistant to a chemical agent if it continues to perform one or more of the physiological functions that a cell of that type normally performs, or if it survives longer in the presence of the chemical agent that is cytotoxic than does a cell whose resistance has not been increased.

Skilled artisans are readily able to determine the circumstances in which it would be desirable to increase the resistance of a cell to a deleterious chemical agent. Generally, these circumstances include any situation in which it is desirable to protect a cell from a chemical agent. For example, it could be desirable to protect certain plants in the vicinity of others that are being treated with an herbicide. Similarity, it could be desirable to protect healthy cells within an animal that are exposed to a chemotherapeutic agent that is administered to treat cancerous cells within the same animal.

The expression of UCH can be increased within a cell in numerous ways, including those described below.

Increasing the Expression of UCH by Transfection with UCH-encoding Nucleic Acid Sequences The expression of UCH within a cell can be increased by transfecting the cell with a nucleic acid molecule that contains a sequence encoding UCH. The sequences encoding many forms of UCH are known, and widely available. These sequences can be ligated into expression vectors and transfected into cells using no more than routine, molecular biological techniques. For example, a nucleic acid sequence encoding UCH can be ligated into a plasmid such as the pMSXND expression vector, which is commonly used to transfect mammalian cells (Lee and Nathans, *J. Biol. Chem.* 263:3521, 1988).

The nucleic acid molecules inserted into the vector may encode a full-length UCH polypeptide, or a biologically active fragment thereof. A biologically active fragment of UCH would be a fragment that can cleave the bond between ubiquitin and a second protein that has been targeted for degradation. Preferably, the encoded polypeptide fragment will exhibit at least 50%, more preferably at least 70%, and most preferably at least 90% (e.g., 95% or even 99%) of the activity of the full-length UCH enzyme of which it was a part. The sequence encoding a biologically active fragment of UCH fragment can, if desired, be obtained by amplifying a region of the full-length UCH nucleic acid molecule by the polymerase chain reaction (PCR), or generated by treating the full-length UCH nucleic acid molecule with one or more restriction endonucleases.

Nucleic acid molecules useful in the practice of the invention can contain either naturally occurring sequences, or sequences that differ from those that occur naturally, but, due to the degeneracy of the genetic code, encode UCH.

The nucleic acid molecule that is inserted into an expression vector can be operably linked to a regulatory sequence, such as that of a promoter or enhancer, which will enhance the expression of the inserted nucleic acid molecule. These regulatory sequences can be those that are naturally associated with genes encoding UCH, i.e., they can include some or all of the non-coding nucleic acid sequence that lies upstream or downstream from a UCH coding sequence in the naturally occurring genome of a eukaryotic cell. Alternatively, the regulatory elements included in the expression vector can be heterologous elements. Cytomegalovirus or metallothionein promoters are commonly used in enhance expression in mammalian cells. In the case of higher eukaryotes, tissue-specific and cell type-specific promoters are also widely available. These promoters are so named for their ability to direct expression of a nucleic acid molecule in a given tissue or cell type that can be maintained in tissue culture or that can be present within the body. Skilled artisans are well aware of numerous promoters and other regulatory elements which can be used to direct expression of nucleic acid molecules.

The recombinant technology required to clone and express such genes is standard in the art and is described in detail, for example, in Sambrook et al. (*Molecular Cloning: A Laboratory Manual,* CSH Laboratory Press, Cold Spring Harbor, N.Y., 1989).

In addition to sequences that facilitate transcription of the inserted nucleic acid molecule, vectors can contain origins of replication, and other genes that encode a selectable or detectable marker. For example, the neomycin-resistance ($neo^r$) gene imparts G418 resistance to cells in which it is expressed, and thus permits phenotypic selection of the transfected cells. Examples of marker or reporter genes include β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). Those of ordinary skill in the art can readily determine whether a given regulatory element or selectable marker is suitable for use in a particular experimental context. Furthermore, and as with many of the standard procedures associated with the practice of the invention, skilled artisans will be aware of additional useful reagents, for example, of additional sequences that can serve the function of a marker or reporter.

Viral vectors can also be used in the invention and include, for example, retroviral, adenoviral, and adeno-associated vectors, herpes virus, simian virus 40 (SV40), and bovine papilloma virus vectors (see, for example, Gluzman (Ed.), *Eukaryotic Viral Vectors,* CSH Laboratory Press, Cold Spring Harbor, N.Y.). If additional guidance is required in creating an expression vector, skilled artisans may consult Ausubel et al. (*Current Protocols in Molecular Biology,* John Wiley and Sons, New York, N.Y., 1993) and Pouwels et al. (*Cloning Vectors: A Laboratory Manual,* 1985 Suppl. 1987).

The nucleic acid molecules of the invention can be synthesized (e.g., by phosphoramidite-based synthesis) or obtained from a biological cell, such as a fungal, plant, or animal cell. Combinations or modifications of the nucleotides within these cell types are also encompassed.

The vectors described above can be used to obtain a transient change in the expression of UCH within a biological cell, or they can be used to incorporate a nucleic acid molecule encoding UCH into the genome of a heterologous cell (or into the genome of a homologous cell, at a position other than the natural chromosomal location).

Those of ordinary skill in the art will understand that there are numerous ways of transfecting biological cells with the nucleic acid molecules described above. For example, cells can be transfected with plasmid vectors by standard methods including, but not limited to, liposome-polybrene-, or DEAE dextran-mediated transfection (see, e.g., Felgner et al., *Proc. Natl. Acad, Sci. USA* 84:7413, 1987; Ono et al., *Neurosci. Lett.* 117:259, 1990; Brigham et al., *Am. J. Med. Sci.* 298:278, 1989), electroporation (Neumann et al. *EMBO J.* 7:841, 1980), calcium phosphate precipitation (Graham et al., *Virology* 52:456, 1973; Wigler et al., *Cell* 14:725, 1978; Felgner et al., supra) microinjection (Wolff et al., *Science* 247:1465, 1990), or velocity driven microprojectiles ("biolistics").

Effective Dose

Toxicity and therapeutic efficacy of a given compound (e.g., UCH or a compound that can alter the level of expression or activity of UCH) can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

Data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulations for Use and Routes of Administration

In therapeutic applications, UCH, or compounds that alter its expression or activity, can be administered with a physiologically-acceptable carrier, such as physiological saline. The therapeutic compositions of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The polypeptides of the invention can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences."

Routes of administration are also well known to skilled pharmacologists and physicians and include intraperitoneal, intramuscular, subcutaneous, and intravenous administration. Additional routes include intracranial (e.g., intracisternal or intraventricular), intraorbital, opthalmic, intracapsular, intraspinal, intraperitoneal, transmucosal, topical, subcutaneous, and oral administration. It is expected that the intravenous route will be preferred for the administration of UCH. The subcutaneous route may also be used frequently as the subcutaneous tissue provides a stable environment for the polypeptide, from which it can be slowly released.

UCH polypeptides, administered according to the methods of the invention, are less likely to be immunogenic than many therapeutic polypeptides because they can be identical to a wild-type polypeptides, i.e., UCH enzymes, within the cell.

It is well known in the medical arts that dosages for any one patient depend on many factors, including the general health, sex, weight, body surface area, and age of the patient, as well as the particular compound to be administered, the time and route of administration, and other drugs being administered concurrently. Dosages for the polypeptide of the invention will vary, but can, when administered intravenously, be given in doses of approximately 0.01 mg to 100 mg/ml blood volume. A dosage can be administered one or more times per day, if necessary, and treatment can be continued for prolonged periods of time, up to and including the lifetime of the patient being treated. If a polypeptide of the invention is administered subcutaneously, the dosage can be reduced, and/or the polypeptide can be administered less frequently. Determination of a correct dosage for a given application is well within the abilities of one or oridnary skill in the art of pharmacology.

Methods for Screening Cytotoxic Agents

Altering the resistance of a cell to cytotoxic agents, by modulating the level of UCH expression or activity, creates a unique population of cells that can be used to screen cytotoxic agents. Cells that have been treated with an agent that increases the expression or activity of UCH, and are therefore more resistant to cytotoxic agents, can be used to identify especially potent cytotoxic agents (i.e., cytotoxins that can kill or otherwise harm cells that have a high level of UCH expression or activity). These agents could be useful in treating cancers that are resistant to presently used chemotherapeutics. A screening method developed on this premise could be carried out as follows. A cell that has been treated with an agent that increased the expression or activity of UCH is contacted with a candidate cytotoxic agent, and the survival of the cell is assessed; a decrease in cell survival would indicate that the candidate cytotoxic agent is a potent cytotoxic agent.

Similarly, weak cytotoxic agents, that could be overlooked in currently available screens, can be identified using cells that have been treated with an agent that decreases UCH expression or activity, and thereby renders the cell more sensitive to cytotoxic agents. Compounds could be screened in this context as follows. A cell that has been treated with an agent that decreases the expression or activity of UCH is contacted with a candidate cytotoxic agent, and the survival of the cell is assessed; a decrease in cell survival indicating the presence of a candidate cytotoxic agent the would have remained undetectable had the cell not been rendered more sensitive to its action (e.g., if the cell had not been treated with an agent that decreases the expression or activity of UCH). Although discovered as a weak cytotoxic agent, those of skill in the art of pharmacology are aware of modifications that could increase the potency of cytotoxic agents discovered according to this method.

Identification of Compounds that Modulate the Expression or Activity of UCH

Also featured in the invention are methods of identifying compounds that increase or decrease the expression or activity of UCH in vivo. For example, to discover such compounds, cells that express UCH are cultured, exposed to a test compound (or a mixture of test compounds), and the level of UCH expression or activity is compared with the level of expression or activity in cells that are otherwise identical but that have not been exposed to the test compound(s). Many standard quantitative assays of gene expression, which are known to those of skill in the art, can be utilized in this aspect of the invention. Virtually any compound can be tested, including small molecule, polypeptides (e.g., oligopeptides, antibodies, or antibody fragments), and nucleic acid molecules. Compounds identified in this way can be used as agents to modulate UCH expression in vivo and, thereby alter the resistance of the treated cell to cytotoxic agents (including, but not limited to doxorubicin, vincristine, colchicine, VP-16, vinblastine, verapamil, mitoxantrone, taxol, Cyclosporin A, quinidine, progesterone, tamoxifen, epirubicin, daunorubicin, MX2, and heavy metal ions such as arsentie, arsenate, antimony tartrate, animonate, and cadmium, whether alone or in any combination).

Following is an example, which is provided for the purpose of illustrating, not limiting, the invention.

EXAMPLE

UCH Expression is Upregulated in Drug-Resistant Cells

Expression of UCTH-L1 was examined in drug-sensitive and drug-resistant UCLA-P3, A2780, and MCF-7 cancer cells by Northern blot analysis, as follows.

Preparation of Drug-Resistant Cells

UCLA-P3 cells were derived from a human non-small cell lung carcinomal. A drug resistant variant, UCLA-P3-0.003VLB cells, was selected in vitro for resistance to 3 ng/ml desacetylvinblastine hemisuccinate over a ten month period of time. Both wild-type and drug resistant cells were cultured in RPMI 1640 containing L-glutamine and 25 mM HEPES buffer (Gibco BRL), supplemented with 10% fetal bovine serum (FBS) and 50 mg/ml gentamycin. The cells were passaged twice weekly by splitting them in ratios of 1:6 or 1:8.

A2780 cells were derived from a human ovarian carcinoma. A doxorubicin resistant variant, 2780AD, was developed by maintaining the A2780 cells in culture with 2 mM doxorubicin (Hamilton et al., *Semin. Oncol.* 11:285–298, 1984). Both the drug-sensitive and drug-resistant cells can be cultured in RPMI medium, as described above, that contains additional L-glutamine (to a final concentration of 2 mM) and 10 $\mu$g/ml bovine insulin.

MCF-7 cells are derived from a human breast carcinoma. Doxorubicin (also known as adriamycin) was used to generate a line of MCF-7 cells that exhibit cross-resistance to a wide range of anti-cancer drugs. This cell line was established by Batist et al. (*J. Biol. Chem.* 261:15544–15549, 1986), as follows. Adriamycin-resistant MCF-7 cells were selected by culturing non-resistant cells in gradually increasing concentrations of adriamycin, with the initial concentration of adriamycin being $10^{-8}$ M. When the cells were able to survive at any given concentration of drug, they were passaged in concentrations that were 1.5-fold to 2-fold higher. The cells finally obtained were able to survive in $10^{-5}$ M adriamycin. In preparation for the experiments described below, drug-sensitive and drug-resistant MCF-7 cells were cultured in RPMI 1640 medium containing L-glutamine, 25 mM HEPES buffer, 10% FBS, and 50 $\mu$g/ml gentamycin.

RNA Extraction and Analysis of UCH Expression

The cell lines described above (i.e., drug-sensitive and drug-resistance MCF-7, A2780, and UCLA-P3 cells) were cultured until confluent, and the culture medium was removed by aspiration and replaced with RLT buffer containing β-mercaptoethanol (1 $\mu$l β-mercaptoethanol/100 $\mu$l RLT buffer; Qiagen), which lyses the cells and stabilizes RNA. The lysates were harvested and homogenized by spinning through a Qiashredder™ column (Qiagen), and the RNA was analyzed by Northern blot.

Figure 1:
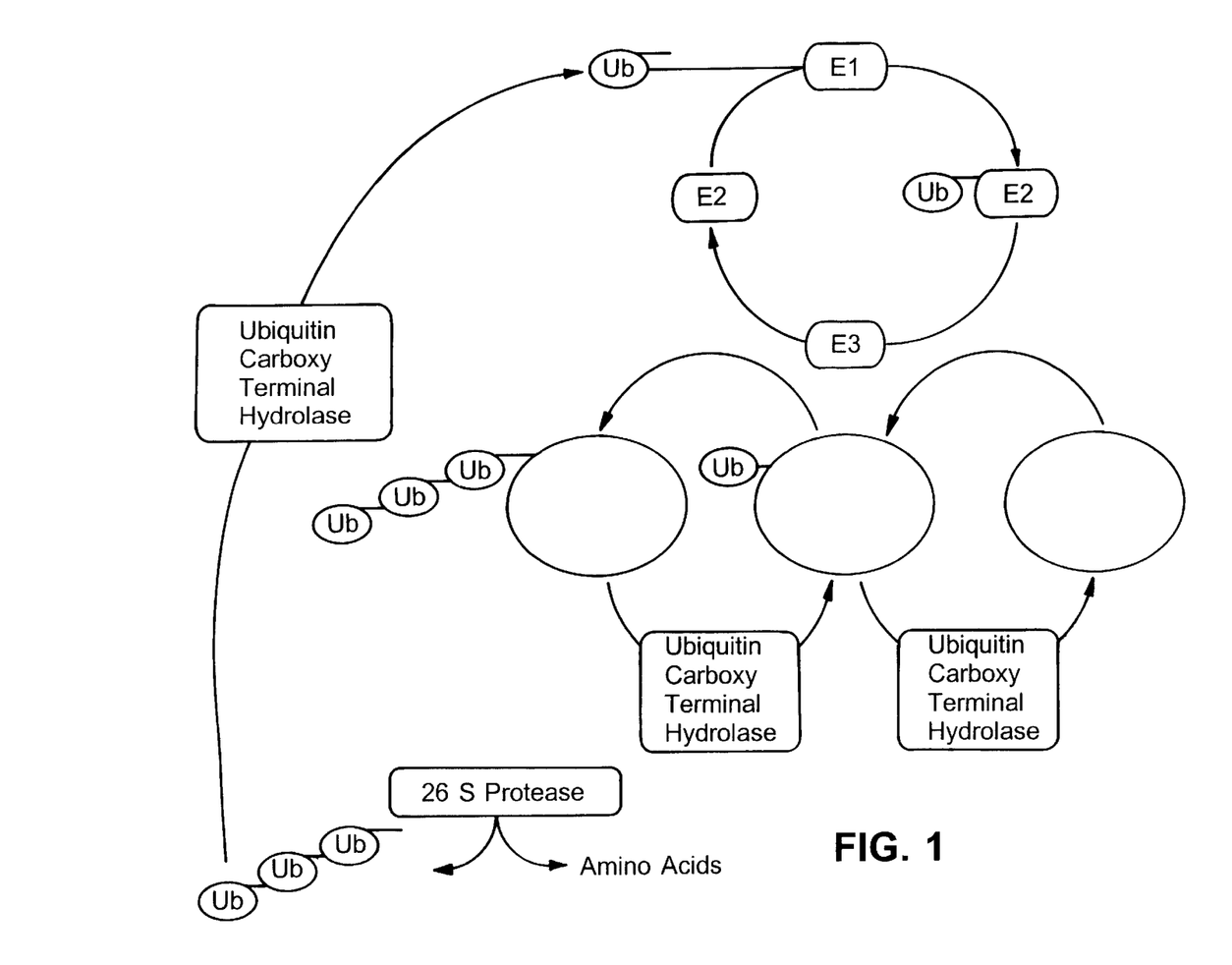
FIG. 1 is a schematic diagram of the ubiquitin pathway.
Figure 2:
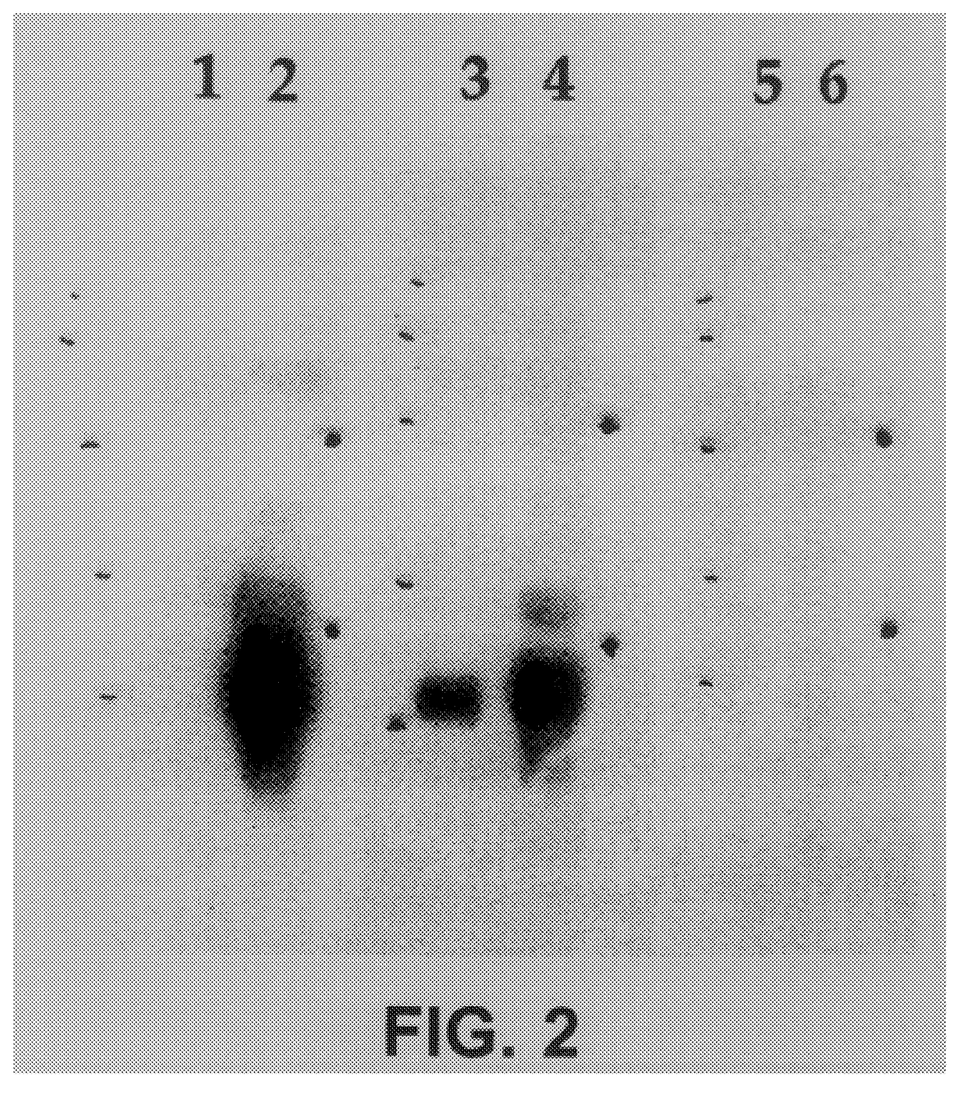
FIG. 2 is a photograph of a Northern blot. Lanes 1–6 contain total RNA collected from the following cells: lane 1, drug-sensitive MCF-7 cells: lane 2, drug-resistant MCF-7 cells; lane 3, drug-sensitive A2780 cells; lane 4, drug-resistant A2780 cells; lane 5, drug-sensitive UCLA-P3cells; and lane 6, drug-resistant UCLA-P3 cells.

As shown in FIG. 2, both drug-resistant MCF-7 cells and drug-resistant A2780 cells showed an upregulation in UCTH-L1 expression compared to their drug-sensitive counterparts. Drug-sensitive A2780 cells exhibit a basal level expression of UCTH-L1 whereas drug-sensitive MCF-7 cells appear to have little or no UCTH-L1 expression. Both drug-resistant and drug-sensitive UCLA-P3 cells failed to show expression of UCTH-L1 message by Northern blot.

What is claimed is:

1. A method for determining whether a patient is suffering from a carcinoma that has become increasingly drug-resistant comprising:
    a) obtaining a first sample comprising carcinoma cells from the patient at a first time;
    b) obtaining a second test sample comprising carcinoma cells from the patient at second time;
    c) measuring the expression of ubiquitin carboxy-terminal hydrolase in the first and second samples; and
    d) determining that the patient is suffering from a carcinoma that has become increasingly drug resistant if the expression of ubiquitin carboxy-terminal hydrolase in the second sample is greater than the expression of ubiquitin carboxy-terminal hydrolase in the first sample.

2. A method for determining whether a patient is suffering from a carcinoma that has become increasingly drug-resistant, the method comprising:
    a) obtaining a first test sample comprising carcinoma cells from the patient at a first time;
    b) obtaining a second test sample comprising carcinoma cells from the patient at second time;
    c) measuring the activity of ubiquitin carboxy-terminal hydrolase in the first and second samples; and
    d) determining that the patient is suffering from a carcinoma that has become increasingly drug resistant if the activity of ubiquitin carboxy-terminal hydrolase in the second sample is greater than the activity of ubiquitin carboxy-terminal hydrolase in the first sample.

3. A method for monitoring the efficacy of a compound for inhibition of drug resistance of carcinoma in a patient, comprising a) obtaining a first sample comprising carcinoma from the patient at a first time;
b) administering the compound to the patient;
c) obtaining a second sample comprising carcinoma from the patient at a second time; and
d) determining the expression of ubiquitin carboxy-terminal hydrolase in the first and second samples; and
e) determining that the compound is effective to inhibit drug resistance of carcinoma cells in the patient when the level of expression of ubiquitin carboxy-terminal hydrolase is lower in the second sample than in the first sample.

4. The method of claim 1 or 3 wherein the level of expression is determined by detecting the amount of mRNA encoding ubiquitin carboxy-terminal hydrolase present in the samples.

5. The method of claim 1 or 3 wherein the level of expression is determined by detecting the amount of ubiquitin carboxy-terminal hydrolase protein present in the samples.

6. A method for monitoring the efficacy of a compound for inhibiting of drug resistance of carcinoma cells in a patient, comprising
a) obtaining a first sample comprising carcinoma cells from the patient at a first time;
b) administering the compound to the patient;
c) obtaining a second sample comprising carcinoma cells from the patient at a second time;
d) determining the activity of ubiquitin carboxy-terminal hydrolase in the first and second samples; and
e) determining that the compound is effective to inhibit drug resistance of carcinoma cells in the patient when the level of activity of ubiquitin carboxy-terminal hydrolase is lower in the second sample than in the first sample.

7. A method for determining whether carcinoma cells of a selected type are drug resistant, comprising
a) obtaining a test sample comprising carcinoma cells of the selected type;
b) determining the level of activity of ubiquitin carboxy-terminal hydrolase in the test sample;
c) comparing the level of activity of ubiquitin carboxy-terminal hydrolase in the test sample with the level of activity of ubiquitin carboxy-terminal hydrolase in a control sample of carcinoma cells of the selected type; and
d) identifying the cells as drug resistant when their is an increased level of activity of ubiquitin carboxy-terminal hydrolase in the test sample compared to the control sample.

8. A method for determining whether carcinoma cells of a selected type are drug resistant, comprising
a) obtaining a test sample comprising carcinoma cells of the selected type;
b) determining the level of activity of ubiquitin carboxy-terminal hydrolase in the test sample;
c) comparing the level of activity of ubiquitin carboxy-terminal hydrolase in the test sample with the level of activity of ubiquitin carboxy-terminal hydrolase in a control sample of carcinoma cells of the selected type; and
d) identifying the carcinoma cells as drug resistant when their is an increased level of activity of ubiquitin carboxy-terminal hydrolase in the test sample compared to the control sample.

9. A method for determining whether treatment with an anti-cancer agent should be continued in a carcinoma patient, comprising:
a) obtaining two or more samples comprising carcinoma cells from the patient during the course of anti-cancer agent treatment;
b) measuring the level of expression of ubiquitin carboxy-terminal hydrolase in the two or more samples; and
c) continuing treatment when the expression level of ubiquitin carboxy-terminal hydrolase does not increase during the course of treatment.

10. The method of claim 9, wherein the level of expression is determined by detecting the amount of mRNA encoding ubiquitin carboxy-terminal hydrolase present in the carcinoma cells.

11. The method of claim 9, wherein the level of expression is determined by detecting the amount of ubiquitin carboxy-terminal hydrolase protein present in the carcinoma cells.

12. A method for determining whether treatment with an anti-cancer agent should be continued in a carcinoma patient, comprising:
a) obtaining two or more samples comprising carcinoma cells from a patient during the course of anti-cancer agent treatment;
b) determining the level of expression of ubiquitin carboxy-terminal hydrolase in the two or more samples; and
c) discontinuing treatment when the expression level of ubiquitin carboxy-terminal hydrolase increases during the course of treatment.

13. The method of claim 12, wherein the level of expression is determined by detecting the amount of mRNA encoding ubiquitin carboxy-terminal hydrolase present in the carcinoma cells.

14. The method of claim 12, wherein the level of expression is determined by detecting the amount of ubiquitin carboxy-terminal hydrolase protein present in the carcinoma cells.

15. A method for determining whether treatment with an anti-cancer agent should be continued in a carcinoma patient, comprising:
a) obtaining two or more samples comprising carcinoma cells from the patient during the course of anti-cancer agent treatment;
b) determining the level of activity of ubiquitin carboxy-terminal hydrolase in the two or more samples; and
c) continuing treatment when the activity level of ubiquitin carboxy-treatment hydrolase does not increase during the course of treatment.

16. A method for determining whether treatment with an anti-cancer agent should be continued in a carcinoma patient, comprising:
a) obtaining two or more samples comprising carcinoma cells from the patient during the course of anti-cancer agent treatment;
b) determining the level of activity of ubiquitin carboxy-terminal hydrolase in the two or more samples; and
c) discontinuing treatment when the activity level of ubiquitin carboxy-terminal hydrolase increases during the course of treatment.

* * * * *

UNITED STATES PATENT AND TRADEMARK OFFICE
CERTIFICATE OF CORRECTION

| | | |
|---|---|---|
| PATENT NO. | : 6,322,982 B1 | Page 1 of 1 |
| DATED | : November 27, 2001 | |
| INVENTOR(S) | : Andrew W. Shyjan and Kyle J. MacBeth | |

It is certified that error appears in the above-identified patent and that said Letters Patent is hereby corrected as shown below:

<u>Column 2,</u>
Line 61, change "comparably" to -- comparable --

<u>Column 5,</u>
Line 2, change "URLS" to -- URLs --
Line 3, change "to" to -- in --
Line 13, change "UCLA-P3cells" to -- UCLA-P3 cells --

<u>Column 8,</u>
Line 42, change "complementarity" to -- complementary --

<u>Column 9,</u>
Line 10, change "lengths" to -- length --

<u>Column 11,</u>
Line 55, change "1989" to -- 1992 --

<u>Column 16,</u>
Line 42, change "or ordinary" to -- of ordinary --

<u>Column 17,</u>
Line 46, change "carcinomal" to -- carcinoma --

<u>Column 18,</u>
Line 66, insert -- cells -- before "in"

<u>Column 19,</u>
Lines 1 and 4, insert -- cells -- before "from"
Lines 49 and 65, change "their" to -- there --

Signed and Sealed this

Second Day of September, 2003

JAMES E. ROGAN
*Director of the United States Patent and Trademark Office*